(12) United States Patent
Chen

(10) Patent No.: US 10,512,411 B2
(45) Date of Patent: Dec. 24, 2019

(54) BRAIN MAPPING SYSTEM AND METHOD THEREOF

(71) Applicant: Chiun-Fan Chen, Brookline, MA (US)

(72) Inventor: Chiun-Fan Chen, Brookline, MA (US)

( * ) Notice: Subject to any disclaimer, the term of this patent is extended or adjusted under 35 U.S.C. 154(b) by 869 days.

(21) Appl. No.: 15/040,420

(22) Filed: Feb. 10, 2016

(65) Prior Publication Data

US 2017/0224241 A1   Aug. 10, 2017

(51) Int. Cl.
*A61B 5/04* (2006.01)
*A61B 5/0484* (2006.01)

(52) U.S. Cl.
CPC ...... *A61B 5/04012* (2013.01); *A61B 5/04008* (2013.01); *A61B 5/0484* (2013.01); *A61B 5/04009* (2013.01)

(58) Field of Classification Search
CPC ............ A61B 5/04008; A61B 5/04009; A61B 5/04012; A61B 5/0484
See application file for complete search history.

(56) References Cited

U.S. PATENT DOCUMENTS

| 6,128,527 A | 10/2000 | Howard, III et al. |
| 8,764,676 B2 | 7/2014 | Prakash et al. |
| 2002/0099295 A1 | 7/2002 | Gil et al. |
| 2008/0046052 A1* | 2/2008 | Werder ............... A61N 1/36017 607/116 |
| 2012/0101547 A1* | 4/2012 | Jensen ............... A61N 1/36067 607/45 |
| 2014/0257128 A1 | 9/2014 | Moxon et al. |
| 2015/0246232 A1 | 9/2015 | Kameneva et al. |
| 2015/0328467 A1* | 11/2015 | Demers ............... A61N 1/36014 607/45 |

* cited by examiner

*Primary Examiner* — Ruth S Smith

(57) ABSTRACT

A brain mapping system includes a brain signal acquisition device for collecting brain signals corresponding to different locations of the brain, a stimulator for generating a stimulus based upon a pseudorandom sequence, and a processor for segmenting the brain signals into a plurality of epochs and correlating features extracted from the epochs with the pseudorandom sequence to generate correlation functions, wherein a brain map is constructed by the correlation functions.

11 Claims, 4 Drawing Sheets

BRAIN MAPPING SYSTEM AND METHOD THEREOF

BACKGROUND OF THE INVENTION

1. Field of the Invention

The invention relates to a brain mapping system and, more particularly, to a brain mapping system constructed by programmed peripheral stimulation.

2. Description of the Related Art

Techniques conventionally used for acquiring brain activity are limited by either their temporal or spatial resolutions and thus are infeasible for real-time monitoring. There is a need to develop more reliable systems with less limitations in order to gain more progress in the field of such clinical applications.

BRIEF SUMMARY OF THE INVENTION

One of the objects of the present invention is to provide a brain mapping system to improve the above-mentioned limitations.

According to an embodiment of the invention, a brain mapping system includes a brain signal acquisition device for collecting brain signals from different locations of the brain, a stimulator for generating a stimulus based upon a pseudorandom sequence, and a processor for segmenting the brain signals into epochs and correlating features extracted from the epochs with the pseudorandom sequence to generate correlation functions.

Moreover, another embodiment of the present invention provides a brain mapping method including the steps of collecting brain signals corresponding to different locations of the brain, generating a stimulus based upon a pseudorandom sequence, segmenting the brain signals into epochs, and correlating features extracted from the epochs with the pseudorandom sequence to generate correlation functions The disclosed brain mapping system and method utilized a pseudorandom sequence to generate correlation functions that are readily available for real-time monitoring of the brain. Such applications will assist other ground-breaking development of clinical applications related to neuroscience.

DETAILED DESCRIPTION OF THE INVENTION

Figure 1:
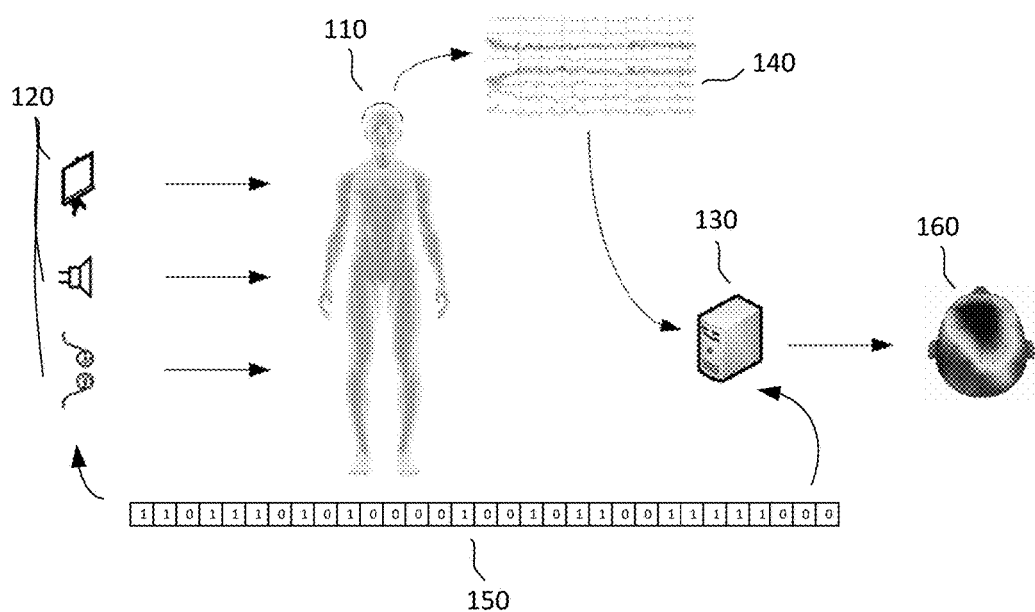
FIG. 1 shows a schematic diagram of a brain mapping system illustrated according to an embodiment of the present invention.

FIG. 1 shows a schematic diagram of a brain mapping system 100 illustrated according to an embodiment of the present invention. The brain mapping system 100 includes a brain signal acquisition device 110, a variety of stimulators 120, and a processor 130. The signal acquisition device 110 includes sensors that collect brain signals 140 corresponding to different locations of the brain. The brain signals 140 can be electroencephalography (EEG) signals and magnetoencephalography (MEG) signals. The stimulators 120 generate a stimulus based upon a pseudorandom sequence 150 (e.g., maximum-length sequence) and is applied via visual, audio, mechanical, optical, or electrical medium. These can be computer screens, computerized goggles, a headphone, speakers, a vibrator, lights, an electrical stimulator or any other device that activates perceptual brain regions. The processor 130 can be a computer, a microprocessor, or application specific integrated circuits that are designed to process brain signals. In a preferred embodiment, the processor 130 processes the brain signals 140 by first filtering and removing artifacts. The processor 130 then segments the brain signals 140 into appropriate epochs and generate specific features from the epochs to correlate with the pseudorandom sequence 150 that generated the stimulus. Examples of the specific features include power, power spectral density, and maximum/minimum values of the epochs. Accordingly, a brain map 160 can be generated by the aforementioned process.

Figure 2:
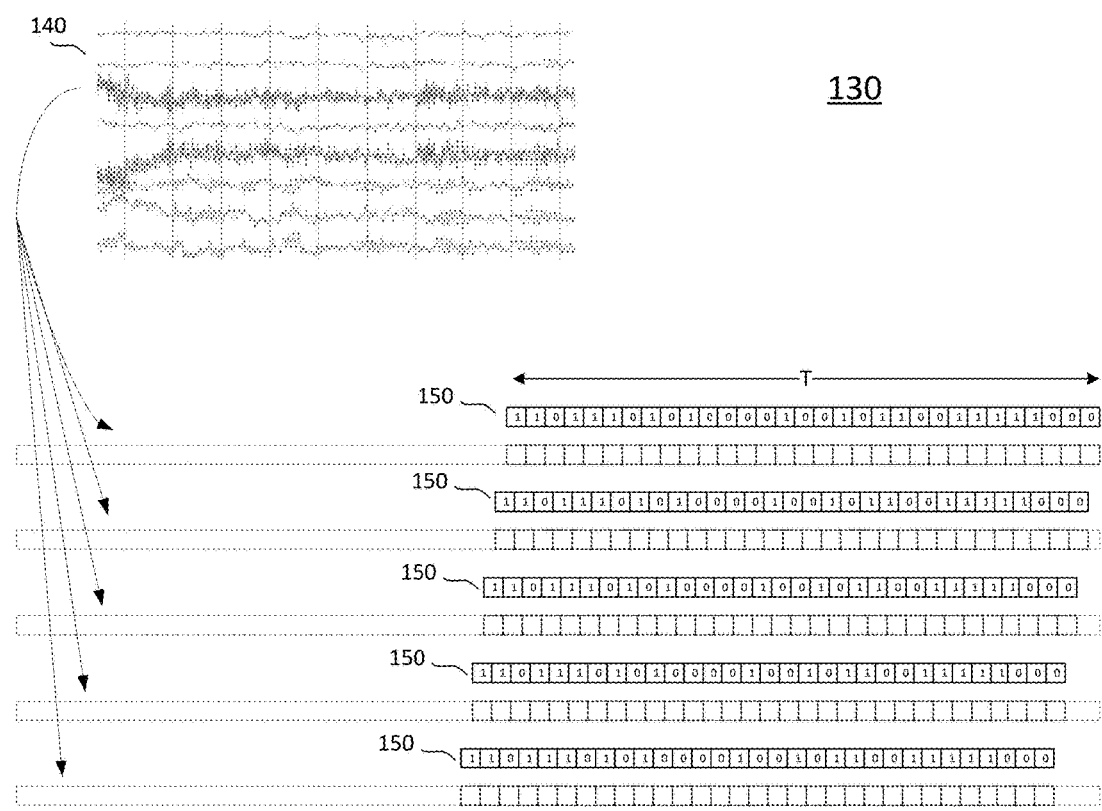
FIG. 2 shows how correlation functions are generated from features extracted from brain signal epochs and a pseudorandom sequence.

An embodiment of the process that takes place in the processor 130 is illustrated in FIG. 2. The pseudorandom sequence 150 shifts along the time axis to correlate with the 1's or 0's derived from the epochs. The epochs are segmented from the brain signals 140 to be substantially equal to the duration of the codes (1's or 0's) in the pseudorandom sequence 150 and the duration of each of the individual codes are also substantially equal. The 1's or 0's derived from the epochs can be determined by comparing the feature of the current epoch with that of earlier epochs. For example, if the power of the current epoch is greater than the mean power of a specific number of prior epochs, a "1" will be assigned to the epoch, otherwise a "0" will be assigned. Please note that the 0's will be converted to −1's for the mathematical procedure of calculating correlation.

Figure 3:
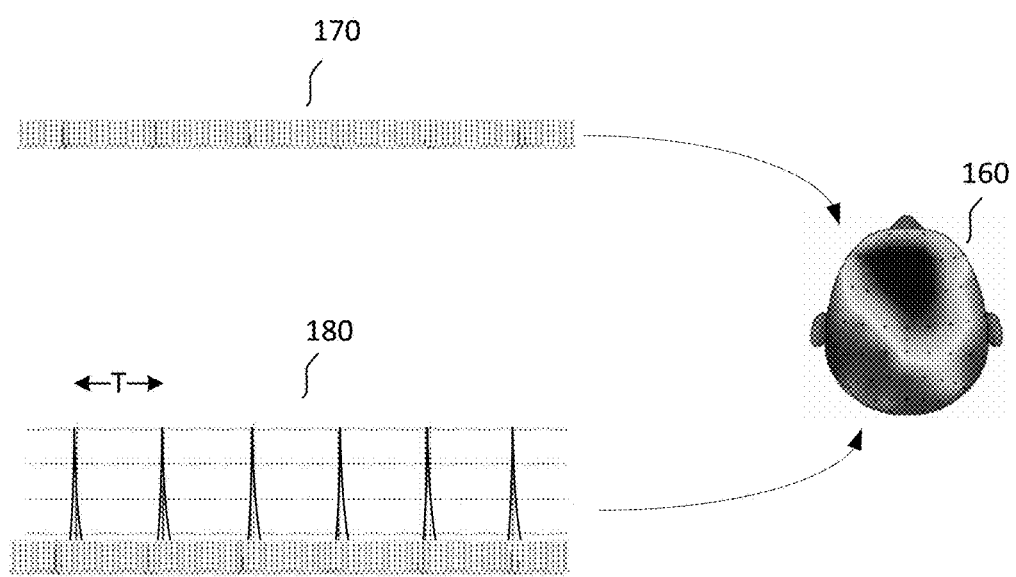
FIG. 3 shows how a brain map is constructed or updated

FIG. 3 is how a correlation function may look like. The correlation function without spikes 170 corresponds to no correlation while correlation function with spikes 180 corresponds to at least some correlation. The more obvious the spikes the greater the correlation. In addition, the spikes are separated by an interval that is substantially equal to the period T of the pseudorandom sequence 150. For example, in the case of a maximum-length sequence, the period T is a single run of the sequence ($2^m-1$ multiplied by the time duration of each code, where m≥3). The extent of correlation can be mapped into the brain map 160.

The stimulus may also cue a motor response (e.g., a muscle contraction or walking gait) and then generate correlation functions that reflect the motor response. Other applications can include navigated brain stimulation that operates with the incorporation of the time-varying brain map. The changes of the brain signals corresponding to the motor or sensory responses will assist in providing the target for brain stimulation, i.e., the brain will be stimulated according to a montage provided by the brain map.

Figure 4:
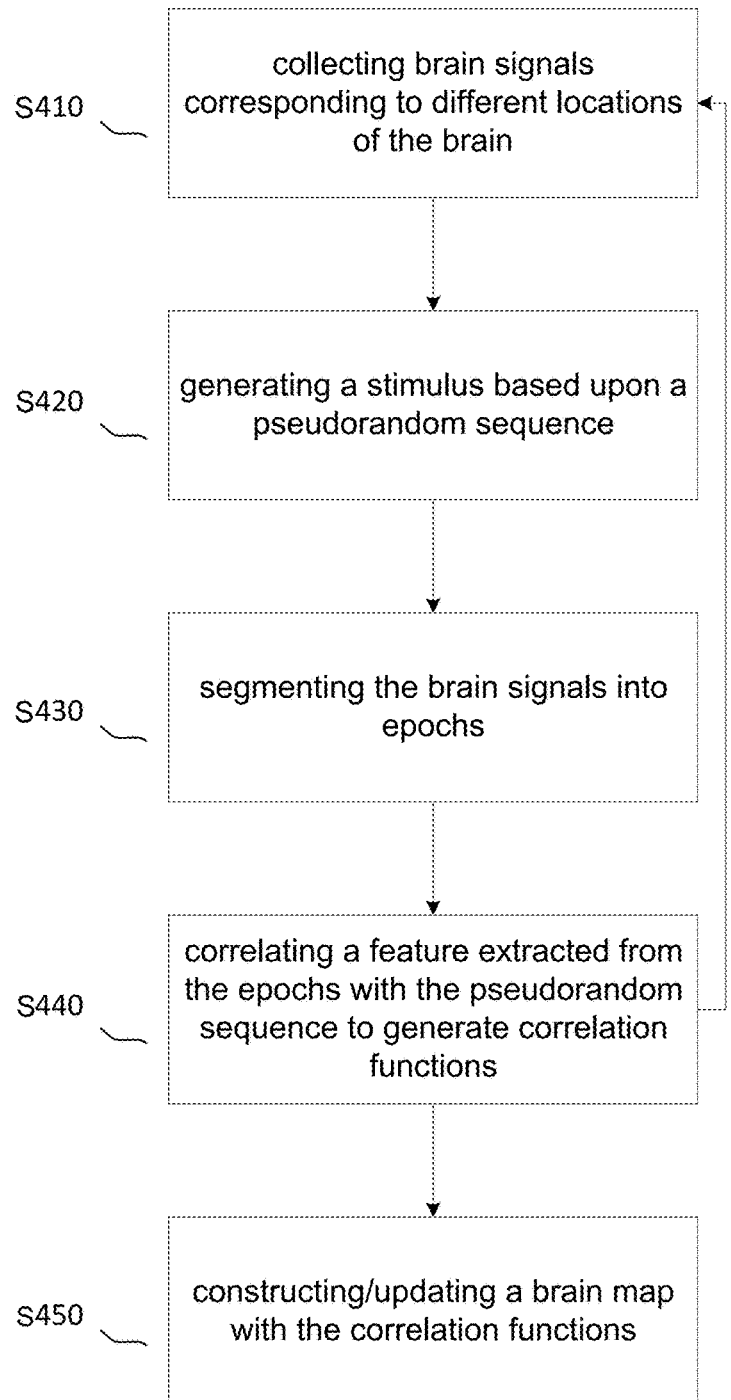
FIG. 4 shows a flow chart of a brain mapping method illustrated according to an embodiment of the present invention.

An embodiment of the present invention is a brain mapping method presented in FIG. 4, which includes the following steps:

Step S410: utilizing sensors to collect brain signals corresponding to different locations of the brain;

Step S420: generating a stimulus based upon a pseudorandom sequence;

Step S430: segmenting the brain signals into epochs;

Step S440: correlating at least one of various features that can be extracted from the epochs with the pseudorandom sequence to generate correlation functions; and Step S450: constructing/updating a time-varying brain map with the correlation functions.

Please note that the time interval between consecutive peaks of at least one of the correlation functions is substantially equal to the period of one run of the pseudorandom sequence.

In some applications of the embodiment, the stimulus may cue a motor response and then generate correlation functions that reflect the motor response. Moreover, the method may be utilized to guide brain stimulation in real time.

While the invention has been described by way of examples and in terms of the preferred embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A brain mapping system, comprising:
   a brain signal acquisition device, comprising sensors that collect a plurality of brain signals corresponding to different locations of the brain;
   a stimulator, generating a stimulus based upon a pseudorandom sequence; and
   a processor, segmenting the brain signals into a plurality of epochs and correlating at least one of a plurality of features extracted from the epochs with the pseudorandom sequence to generate a plurality of correlation functions that last more than two runs of the pseudorandom sequence;
   wherein a brain map is constructed by correlation values between the pseudorandom sequence and the brain signals corresponding to different locations of the brain.

2. The brain mapping system of claim 1, wherein the time interval between peak correlation values of the correlation functions is substantially equal to the period of one run of the pseudorandom sequence.

3. The brain mapping system of claim 1, wherein the stimulus is visual, audio, mechanical, optical, or electrical.

4. The brain mapping system of claim 1, wherein the stimulus cues a motor response.

5. The brain mapping system of claim 1, wherein the processor is comprised of an application specific integrated circuit.

6. The brain mapping system of claim 1, wherein the features comprise power, power spectral density, and maximal voltage.

7. The brain mapping system of claim 1, further comprising a brain stimulation device that stimulates the brain according to a montage provided by the brain map.

8. A brain mapping method, comprising the steps of:
   utilizing sensors to collect a plurality of brain signals corresponding to different locations of the brain;
   generating a stimulus based upon a pseudorandom sequence;
   segmenting the brain signals into a plurality of epochs; and
   correlating at least one of a plurality of features extracted from the epochs with the pseudorandom sequence to generate a plurality of correlation functions that last more than two runs of the pseudorandom sequence;
   wherein a brain map is constructed by correlation values between the pseudorandom sequence and the brain signals corresponding to different locations of the brain.

9. The brain mapping method of claim 8, wherein the time interval between peak correlation values of the correlation functions is substantially equal to the period of one run of the pseudorandom sequence.

10. The brain mapping method of claim 8, wherein the stimulus cues a motor response.

11. The brain mapping method of claim 8, further comprising the step of stimulating the brain according to a montage provided by the brain map.

* * * * *